United States Patent [19]

Greenwald et al.

[11] Patent Number: 4,908,381
[45] Date of Patent: Mar. 13, 1990

[54] ANTIMICROBIAL FILM-FORMING COMPOSITIONS

[75] Inventors: Richard B. Greenwald, Eagan; Isaac S. Y. Sze, St. Paul, both of Minn.

[73] Assignee: Ecolab Inc., St. Paul, Minn.

[21] Appl. No.: 279,536

[22] Filed: Dec. 5, 1988

[51] Int. Cl.$^4$ .................... A01N 43/16; C07D 315/00
[52] U.S. Cl. ..................................... 514/460; 549/417
[58] Field of Search .................. 424/78; 549/417; 514/460

[56]  References Cited

U.S. PATENT DOCUMENTS

| | | | |
|---|---|---|---|
| 2,443,496 | 4/1945 | Flodin | 260/86 |
| 2,514,172 | 7/1950 | Whetstone et al. | 260/333 |
| 2,619,491 | 11/1952 | Smith | 260/333 |
| 2,689,837 | 9/1954 | Darby et al. | 260/30.8 |
| 2,873,263 | 2/1959 | Lal | 260/45.4 |
| 2,875,097 | 2/1959 | Pritchard | 117/138.5 |
| 2,877,208 | 3/1959 | Lal | 260/45.5 |
| 3,325,436 | 6/1967 | Prindle et al. | 260/29.7 |
| 3,389,112 | 6/1968 | Nordstrom | 260/30.4 |
| 3,479,249 | 11/1969 | Stapleton | 161/218 |
| 3,480,678 | 11/1969 | Thweatt | 260/594 |
| 3,577,516 | 5/1971 | Gould et al. | 424/46 |
| 3,637,760 | 1/1972 | Dowbenko | 260/345.8 |
| 3,723,398 | 3/1973 | Dowbenko | 260/80.72 |
| 3,872,109 | 3/1975 | Furrer et al. | 260/343.5 |
| 3,873,500 | 3/1975 | Kato et al. | 260/47 |
| 3,893,985 | 7/1975 | Papa et al. | 260/80.3 |
| 3,966,902 | 6/1976 | Chromacek | 424/59 |
| 3,969,323 | 7/1976 | Furrer et al. | 260/73 R |
| 4,568,734 | 2/1986 | Tan et al. | 526/266 |

FOREIGN PATENT DOCUMENTS 672947 10/1963 Canada.

OTHER PUBLICATIONS

CA 107: 1154572, Malanga et al, "A New Approach to δ lactmes, Releated to Prelog-Djerassi Lactone", 1987.
C. W. Smith et al., J. Amer. Chem. Soc., 74, 2018 (1952).
J. E. Kearns et al., J. Macromol. Sci.-Chem., A8(4), 673 (1974).
L. Malanga et al., Tetrahedron Letters, 28, 239 (1987).

Primary Examiner—Joseph L. Schofer
Assistant Examiner—Pili Curtis
Attorney, Agent, or Firm—Merchant, Gould, Smith, Edell, Welter & Schmidt

[57]  ABSTRACT

The present invention provides a liquid composition that yields an abrasion resistant polymeric film on a surface that provides extended protection from microbial growth through slow release of a potent antimicrobial agent. The active ingredient of the liquid composition has the following general formula:

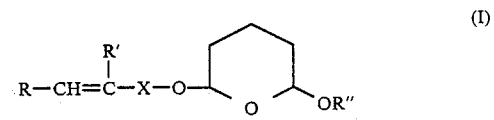

wherein
R=H, (C$_1$–C$_3$)alkyl, —COOH, —CH$_2$—COOH, —C$_6$H$_{11}$, or -phenyl;
R'=H, (C$_1$–C$_3$)alkyl, —CH$_2$—COOH, —C$_6$H$_{11}$, or -phenyl;
R''=H, or (C$_1$–C$_5$)alkyl; and
X=a single bond;

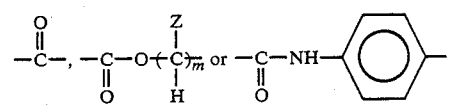

where
m=2–4; and
Z=H or (C$_1$–C$_3$)alkyl; as well as homopolymers, copolymers, or terpolymers comprising said active ingredient.

10 Claims, 1 Drawing Sheet (II)

(III)

(IV)

(V)

(VI)

(VII)

(II)

(III)

(IV)

(V)

(VI)

(VII)

ANTIMICROBIAL FILM-FORMING COMPOSITIONS

FIELD OF THE INVENTION

The invention relates to antimicrobial compositions, and particularly to liquid antimicrobial compositions that yield adherent, transparent, abrasion resistant polymeric films having prolonged antimicrobial properties.

BACKGROUND OF THE INVENTION

Studies have indicated that the contamination of both wet and dry household surfaces with potentially pathogenic quantities of bacteria is widespread. Following a study of bacterial flora in 200 homes, Scott et al., in *J. Hyg. Camb.*, Vol. 89, 279 (1982), concluded that improved decontamination procedures are necessary, particularly at sites which are repeatedly wetted, such as the surfaces of sinks, toilets, draining boards, stoves, washing machines, and the like. However, controlled in-use tests employing dilute aqueous detergents at kitchen and bathroom sites achieved no observable reduction in microbial contamination, while application of aqueous hypochlorite and phenolic disinfectant compositions only produced a significant reduction in contamination levels for 3-6 hours. In their evaluation of disinfectants in the domestic environment, Scott et al., *J. Hyg. Camb.*, Vol. 92, 193 (1984), hypothesized that the rapid recontamination was due both to fresh contamination of surfaces, such as toilets, and to the local multiplication of residual colonies at repeatedly wetted sites, such as sinks.

Compositions intended for the controlled release of a disinfectant from a film of a stabilized hydrophilic polymer are disclosed in U.S. Pat. No. 3,966,902. The polymer complex is stabilized as a metal complex by the addition of an inorganic aluminum, zirconium or zinc salt, such as aluminum chlorohydrol, to the polymerization mixture. The stabilization adjuvant is necessary because upon contact with water, films of simple hydrogels become highly swollen and rapidly elute their additives. Furthermore, dry films, both simple and metal-complexed hydrogels, do not adhere well to ceramic and other hard surfaces and can lose their adhesion completely when wetted.

Other antimicrobial agents have been combined with film-forming polymeric materials to accomplish various ends. For example, U.S. Pat. No. 3,325,436 discloses bacteria resistant latexes that incorporate α,α'-azobis(chloroformamidine). Similarly, U.S. Pat. No. 2,689,837 discloses polymeric vinyl halides having improved resistance to deterioration caused by fungal and bacterial attack, which incorporate copper 8-quinolinolate into the polymer. Also, U.S. Pat. No. 3,577,516 discloses a spray-on bandage material using acrylate or methacrylate polymers that may contain germicides or fungicides.

Phenols and thiophenols are known antimicrobial agents that have been incorporated into polymeric compounds. U.S. Pat. No. 2,875,097 discloses the incorporation of phenolic compounds into polymers comprising heterocyclic nitrogen compounds. These polymers are used to render fabrics resistant to fungi and insects. U.S. Pat. No. 2,873,263 discloses an antibacterial polymeric resin used for fabricating plastic articles. These resins are formed by polymerizing an unsaturated monomer, such as an aklyl acrylate, in the presence of certain aromatic phenols or thiophenols.

However, the incorporation of various biocides into polymeric base materials, either by physical entrapment or by ionic complexation, has not satisfactorily addressed the problem of providing a polymeric composition capable of forming thin, stable films that exhibit potent, prolonged antimicrobial action. Therefore, a continuing need exists for an antimicrobial composition capable of forming a polymeric film that can release a biodegradable, antimicrobial agent in sufficient concentrations to provide a surface substantially free of microorganisms. A need also exists for an antimicrobial polymeric film capable of providing a surface with prolonged resistance to microbial growth.

BRIEF DESCRIPTION OF THE INVENTION

The present invention provides a liquid composition that, when applied to a target surface, yields an abrasion resistant polymeric film. The film protects the surface from microbial growth through the slow release of a potent antimicrobial agent.

The present invention provides an antimicrobial composition comprising a compound having the following general formula:

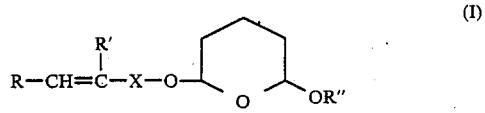

(I)

wherein

R=H,($C_1$-$C_3$)alkyl,—COOH,—$CH_2$—COOH,—$C_6H_{11}$, or -phenyl;

R'=H,($C_1$-$C_3$)alkyl,—$CH_2$—COOH,—$C_6H_{11}$, or -phenyl;

R''=H,($C_1$-$C_5$)alkyl; and

X=a single bond,

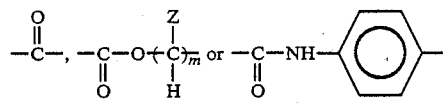

where:

M=2-4; and

Z=H or $C_1$-$C_3$ alkyl.

Preferably R=H or ($C_1$-$C_3$)alkyl; R'=H or ($C_1$-$C_3$); R''=H or ($C_1$-$C_3$)alkyl; and X=

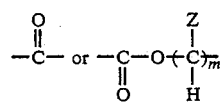

where:

m=2; and

Z=H or ($C_1$-$C_3$)alkyl;

Most preferably R=H; R''=H or —$CH_3$; R''=—$CH_3$; and

X=

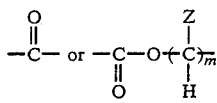

where:
m=2; and
Z=H or —CH₃.

Compound I can be dissolved in a suitable solvent and the resultant solution used directly as a liquid sanitizing composition. Alternatively, it may be used as a monomer and polymerized to form a homopolymer. When dissolved in a suitable solvent and applied to a surface, the polymer also yields an antimicrobial film. The liquid composition may be applied to a surface by spraying, wiping, pouring, and the like. The resultant films are clear, adherent, and are resistant to abrasion in the sense that they are not readily removed when the surface is wiped or sprayed with water.

Compound I can also be polymerized with other compounds to yield a copolymer, or an oligopolymer. Preferably, Compound I is copolymerized with an alpha, beta-unsaturated carboxylic acid ester selected from the group consisting of aromatic esters, cycloalkyl esters, alkyl esters, (hydroxy)alkyl esters and (alkoxy)alkyl esters; with an alpha, beta-unsaturated amide; or with an alpha,beta-unsaturated carboxylic acid. A terpolymer may be formed, for example, from Compound I, an alpha,beta-unsaturated carboxylic acid ester, and an alpha,beta-unsaturated carboxylic acid. Likewise, when dissolved in a suitable solvent and applied to a surface, the co- and terpolymers yield self-sanitizing films.

The invention also includes a method of disinfecting a surface comprising applying to the surface Compound I, or a polymer thereof, dissolved in a suitable solvent.

Although not wishing to be bound by any theory of action, it is believed that the desirable properties of the invention are due to the ability of Compound I, or of a polymeric film derived therefrom, to release the potent antimicrobial agent, glutaraldehyde, upon contact with water. It is believed that residual amounts of acid present in the polymeric film aid in the release of glutaraldehyde. The glutaraldehyde is released over a prolonged period of time. As used herein, "a prolonged period of time" means at least one week and preferably more than three weeks.

DETAILED DESCRIPTION OF THE INVENTION

Application of Abrasion Resistant Film

Figure 1:
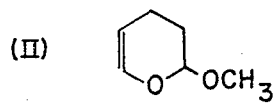
FIG. 1 depicts the chemical structures of a compound used as a starting material (II) and various compounds of the present invention (III–VII).
Figure 1:
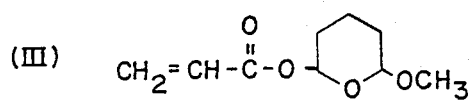
Figure 1:
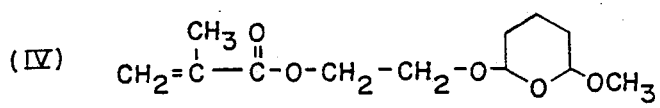
Figure 1:
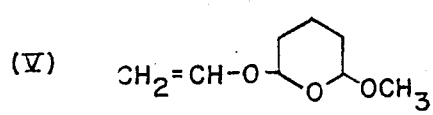
Figure 1:
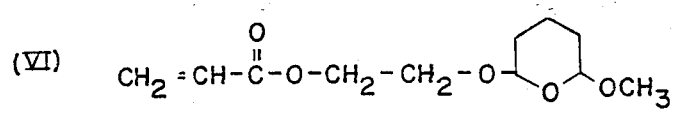
Figure 1:
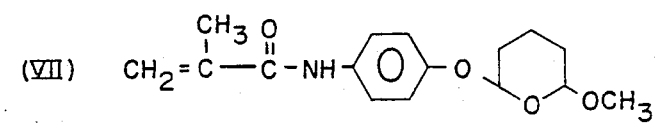

A surface that is coated with an antimicrobial film of the invention will be essentially self-sanitizing. Coatings of the instant antimicrobial composition on surfaces found in homes, hospitals, schools, and the work place will be useful to combat diseases that can be spread by a wide variety of microorganisms.

The instant antimicrobial composition may be applied to a surface in a number of ways. The antimicrobial compound can be dissolved in a suitable solvent, preferably an organic solvent. In polymers comprising a monomer having a free —CO₂H group, the material can be dissolved in water, if the —CO₂H group is partially or totally neutralized with an appropriate base. The instant antimicrobial composition can be applied to a surface by a number of methods including wiping the composition onto a surface with a cloth or sponge; pouring the composition onto a surface and spreading it with a mop, squeegee, sponge, or cloth; dispensing the composition from a container equipped with a pump spray mechanism; dispensing the composition propelled by an aerosol from a suitable pressurized container; and providing the composition in sufficient concentrations on a cloth or other absorbent carrier, and packaging the premoistened carriers for disposable use.

Hard surfaces suitable for coating with the instant polymeric films include surfaces composed of refractory materials, such as glazed and unglazed tile, brick, porcelain, ceramics, metals, glass; and hard plastics, such as formica, polystyrenes, vinyls, acrylics, polyesters, and the like.

The liquid composition is preferably coated at a thickness sufficient to form a residual film of about 0.01–5 mm.

Monomer

Compound I can be formed by combining an alkoxy dihydropyran, such as 3,4-dihydro-2-methoxy-(2H)pyran, 3,4-dihydro-2-ethoxy-(2H)pyran, or 3,4-dihydro-2-propoxy-(2H)pyran with an alpha,beta-unsaturated carboxylic acid, such as acrylic, methacrylic, itaconic, aconitic, cinnamic, crotonic or mesaconic acid, or with a hydroxyalkyl acrylate, such as (2-hydroxyethyl)methacrylate, (2-hydroxyethyl)ethacrylate, (2-hydroxyethyl)acrylate, (3-hydroxypropyl)methacrylate, or (3-hydroxypropyl) ethacrylate, with acid catalysis, with or without the use of an inert solvent.

Compound I monomer can be formed into a liquid disinfectant simply by dissolving it in a suitable solvent. Suitable solvents include organic solvents, such as ($C_2$-$C_4$)alkanols; lower ketones, such as acetone; methyl ethyl ketone; ethyl acetate; tetrahydrofuran (THF); and the like. Organic solvents can also be mixed with compatible amounts of water. Preferred solvents are nontoxic and odorless. The useful disinfecting concentration of Compound I is dependent on the desired end use, but is typically about 0.5–50 wt% of the total solution.

Homopolymer

Compound I may be homopolymerized to form a film-forming polymer. The resultant film has prolonged anti-microbial properties. The homopolymer, as well as the copolymers and terpolymers described below, can be prepared by carrying out the polymerization of the monomers in a solvent or solvent mixture and at concentrations wherein the resultant polymers remain in solution. Preferred solvents include lower alkanols, such as ethanol; ketones, such as acetone; glycol esters or ethers; lower (alkyl)acetates; tetrahydrofuran; dimethylformamide; and the like. The monomeric starting materials are typically dissolved in the solvent to the desired concentration, e.g., to a total concentration of about 10–35% by weight, although somewhat higher or lower concentrations may be employed in some cases.

The polymerization reaction is initiated in the conventional manner, preferably by use of a suitable initiator. Examples of suitable initiators include 2,2'-azobis[2-methylpropanenitrile](AIBN), dibenzoyl peroxide, tert-butyl peroctoate, cumene hydroperoxide, diisopropyl percarbonate, ammonium persulfate, and the like, per se, or in combination with a reducing agent, in the form of an oxidation-reduction system.

During the course of the reaction, the reaction mixture may be agitated and heated, preferably under an inert atmosphere, to about 50°–100° C., preferably to about 75°–95° C. After completion of the polymerization reaction, a solution of polymer results, which can be applied to the target surface without further purification or concentration, or can be collected and redissolved in another solvent.

Copolymerization

Compound I can be copolymerized with alpha,beta-unsaturated carboxylic acids, such as methacrylic acid, acrylic acid, itaconic acid, aconitic acid, cinnamic acid, crotonic acid, mesaconic acid, maleic acid, fumaric acid, and the like. The preferred carboxylic acid comonomers are methacrylic acid, acrylic acid, and itaconic acid. Compound I is typically present in said copolymers at about 40–95% by weight of the copolymer. The carboxylic acid comonomer typically is present in a concentration of about 5–60% by weight, and preferably about 10–45% by weight, of the total polymer.

In addition, Compound I may be copolymerized with alpha,beta-unsaturated carboxylic acid esters of the carboxylic acids described above. Such esters include as aromatic esters, cycloalkyl esters, alkyl esters, (hydroxy)alkyl esters or (alkoxy)alkyl esters. The carboxylic acid ester comonomer typically is present in a concentration of about 5–60% by weight, and preferably about 10–45% by weight of the total polymer.

As used herein, the term "cycloalkyl ester" includes mono-, bi- and tricycloalkyl esters, and the term "aromatic ester" includes heteroaromatic esters. Especially preferred cycloalkyl and aromatic esters are those of acrylic acid, methacrylic acid, or itaconic acid. Useful aromatic esters of these acids include phenyl, benzyl, tolyl, tetrahydrofurfuryl, and phenoxyethyl esters. Useful cycloalkyl esters include ($C_5$–$C_{12}$) cycloalkyls, e.g., the cyclohexyl, cyclopentyl, isobornyl, and adamantyl esters of these acids.

Preferred (hydroxy)alkyl ester comonomers include (2-hydroxyethyl)methacrylate, (2-hydroxyethyl)ethacrylate, (2-hydroxyethyl)acrylate, (3-hydroxypropyl)methacrylate, (3-hydroxypropyl)acrylate, or (3-hydroxypropyl)ethacrylate.

Alkyl and (alkoxy)alkyl esters of alpha, beta-unsaturated carboxylic acids can be used in combination with the aromatic and/or cycloalkyl ester. Preferably the alkyl esters will be selected from higher alkyl esters, such as those of about 5–22 carbon atoms, most preferably about 7–12 carbon atoms.

The alkyl and (alkoxy)alkyl esters of acrylic acid, methacrylic acid and itaconic acid are preferred for use as comonomers.

Examples of useful ($C_5$–$C_{12}$)alkyl ester include hexyl, octyl, ethyl(hexyl), isodecyl, and lauryl acrylates, methacrylates, and itaconates. Examples of (alkoxy)alkyl esters useful as comonomers include ($C_1$–$C_4$)alkoxy-($C_1$–$C_4$)alkyl esters of acrylic, methacrylic or itaconic acid such as (methoxy)ethyl, (ethoxy)ethyl, (methoxy)propyl, (ethoxy)propyl, and the like.

Examples of suitable esters include: (2-hydroxyethyl)acrylate or methacrylate, (hydroxypropyl) acrylate or methacrylate, (dimethylaminoethyl)methacrylate, (piperidinoethyl)methacrylate, (morpholinoethyl) methacrylate, methacrylylglycolic acid, the monomethacrylates of glycol, glycerol, and of other polyhydric alcohols, the monomethacrylates of dialkylene glycols and polyalkylene glycols.

Alpha,beta-unsaturated amides may also be copolymerized with Compound I, including acrylamide, methacrylamide, diacetone acrylamide, methylolacrylamide, methylolmethacrylamide, and the like.

Terpolymer

Compound I may be reacted with two different coreactants to form a terpolymer, which when dissolved in a solvent and coated on a surface forms an abrasion resistant polymeric film having prolonged antimicrobial properties. For example, a terpolymer is formed with (a) Compound I; (b) an alpha,beta-unsaturated carboxylic acid; and (c) an alpha,beta-unsaturated carboxylic acid ester or an alpha,beta-unsaturated amide. Each of these components is present at a concentration of about 5–60% by weight, preferably about 10–45% by weight of the total polymer. Suitable and preferred alpha,beta-unsaturated carboxylic acids, acid esters, and amides include those described under "Comonomers" above.

The invention will be further described by reference to the following detailed examples.

EXAMPLE 1

Synthesis of 2-Methoxytetrahydropyran-6-yl acrylate (III)

Compound III was prepared as follows: 3 drops of methanesulfonic acid was added to a mixture of 57 ml of Compound II and 17.5 ml of acrylic acid under an atmosphere of nitrogen. The temperature rose to about 55° C. and dropped to room temperature over a two hour period, at which point the reaction was stopped by stirring the mixture with a solution of 2 g of potassium carbonate in 4 ml of water. After the two phases separated, the organic phase was vacuum distilled in the presence of a small amount of hydroquinone. The first fraction was unreacted Compound II and distilled at about 25° C.; Compound III at about 58° C. (0.15 mm Hg). The yield of Compound III was about 60%. The structure was in agreement with the following data:

IR: 1730 (ester), 1635 (C=C), 1010 (substituted tetrahydropyran ring) $cm^{-1}$;

$^{13}$C—NMR 164.7, 131.7, 129.5, 100.3, 91.5, 55.6, 30.2, 29.8, 17.9 ppm. The latter also showed the product to be a mixture of two (cis and trans) isomers.

EXAMPLE 2

Synthesis of 2-(2-methoxytetrahydropyran-6-oxy)ethyl-2-methyl-2-propenoate (IV)

Compound IV was prepared as follows: to a mixture of 180 ml of anhydrous diethyl ether, 30 ml of Compound II, and 3 drops of methane sulfonic acid under an atmosphere of nitrogen, 32 ml of (2-hydroxyethyl)methacrylate was added dropwise over a 20 minute period. Throughout the 48 hour reaction time, the reaction mixture was maintained at room temperature. The reaction mixture was then washed once with 250 ml of 0.1 N sodium hydroxide, and then twice with 250 ml of water. After drying the ether phase over anhydrous potassium carbonate, filtering and evaporating the solvent under vacuum, the product was obtained as a light yellow oil. The yield of Compound IV was about 80%. The structure was in agreement with the following data: p IR: 1721 (ester), 1636 (C=C), 1010 (substituted tetrahydropyran ring) $cm^{-1}$;

$^{13}$C—NMR: 167.3, 137.4, 125.7, 99.2, 98.1, 66.2, 64.6, 55.4, 30.9, 30.9, 18.7, 18.2 ppm. The latter also showed the product to be a mixture of two (cis and trans) isomers.

EXAMPLE 3

Synthesis of 6-Ethylenoxy-2- methoxytetrahydropyran (V)

Compound V was made in a two step process. 6-(2-bromoethoxy)-2-methoxytetrahydropyran was made as follows: 2-bromoethanol (62.49 g, 0.50 mole) was added to 500 ml of anhydrous diethyl ether followed by 114.14 g (1.00 mole) of 3,4-dihydro-2-methoxy-(2H)pyran. The flask was flushed with N$_2$ as 3 drops of methane sulfonic acid catalyst were added. The solution was stirred overnight under N$_2$. The reaction solution was concentrated on a rotary evaporator (to drive the reaction to completion) before diluting again with 500 ml of ether. This solution was then extracted with 400 ml of H$_2$O (pH 9). The ether phase was then dried over K$_2$CO$_3$ and the ether removed in vacuo. The evaporation was discontinued when the pressure reached 15 mm Hg. This gave 152.5 g of product, the excess being unreacted 3,4- dihyro-2-methoxy-(2H)pyran.

Next, 6-ethenyloxy-2-methoxytetrahydropyran (V) was made as follows: 152.5 g of crude 6-(2-bromoethoxy)-2-methoxytetrahydropyran was added to a 500 ml round-bottomed flask, purged with N:, as 300 ml of dry tetrahydrofuran (THF) was added. Next, 100 g (0.89 mole) of potassium t-butoxide was added over a one hour period while the temperature was maintained at between 10°-20° C. with an icebath. Once the addition was complete, the bath was heated until the reaction solution reached 45° C. and the temperature of the solution was maintained for 15 minutes. The solution was then added to 300 ml of ice, followed by the addition of 100 g of KCl and 200 ml of H$_2$O with thorough stirring. This two phase solution was added to a two liter separatory funnel and 200 ml of diethyl ether was added to extract the crude product. The organic phase was dried over K$_2$CO$_3$, with vigorous stirring. The solvents were evaporated in vacuo and vacuum distilled (bp 45° C./0.3 mm Hg) to yield 68.00 g of Compound V, (86% yield, overall) as a clear, colorless oil. Infrared (IR) and carbon-13 nuclear magnetic resonance ($^{13}$C—NMR) analysis yielded the following results:

IR: 2940, 1645, 1452, 1435, 1183, 1110, 1008, 940, 883 cm$^{-1}$;

$^{13}$C—NMR: 149.9, 99.03, 97.62, 91.18, 55.69, 30.66, 29.90, 17.88 ppm.

EXAMPLE 4

Synthesis of 2-(2-methoxytetrahydropyran-6-oxy) ethyl-2-propenoat (VI)

Compound VI was made as follows: ethylene glycol (310.0 g, 5.00 moles) was heated to 60° C. before beginning the dropwise addition of 2-chloropropanoyl chloride (127.0 g, 1.00 mole) dissolved in 300 ml of anhydrous diethyl ether. The reaction was exothermic and the temperature rose to 65° C. The ether was allowed to boil off throughout the reaction. The reaction was heated to maintain 65° C. throughout the latter part of the addition and for 30 minutes after completion. The reaction solution was separated into two 250 ml batches that were added separately to 400 ml of H$_2$O and extracted three times with 200 ml of hexane. The hexane extract was discarded and the aqueous phase was saturated with potassium chloride and extracted three times with 200 ml of ethyl acetate. The ethyl acetate was evaporated in vacuo and the concentrate was diluted with 300 ml of diethyl ether and dried over a mixture of anhydrous potassium carbonate and magnesium sulfate. After removing the solvent, the oil was vacuum distilled to give 109.4 g (71.0% yield) of approximately 95% pure 2-hydroxyethyl-2-chloropropanoate. The colorless, clear liquid had a boiling point of 85°-87° C./0.20 mm Hg. The structure of the compound was in agreement with the following data:

IR: 3400, 2950, 1740, 1385, 1080 cm$^{-1}$;

$^{13}$C—NMR: 172.4, 67.66, 61.60, 40.96, 38.79 ppm.

To a solution of 3,4-dihydro-2-methoxy-(2H)pyran (52.0 g, 0.45 mole) in 250 ml of anhydrous diethyl ether, 34.8 g (0.23 mole) of 2-hydroxyethyl-2-chloropropanoate was added. The reaction flask was flushed with dry N$_2$, as four drops of methane sulfonic acid catalyst were added. The reaction solution was stirred overnight at room temperature (approximately 16 hours). The reaction mixture was added to 180 ml of water (pH 9) and extracted twice with 150 ml of diethyl ether. After removing solvent, 48.0 g (80% yield) of approximately 80% pure (2-(2-methoxytetra- hydropyran-6-oxy)ethyl)-3-chloropropanoate was recovered. The structure was in agreement with the following data:

IR: 2950, 1740, 1390, 1120, 1010 cm$^{-1}$;

$^{13}$C—NMR 171.7, 100.3, 99.03, 67.12, 65.66, 56.40, 41.12, 39.11, 31.80, 19.12 ppm.

To a solution of 70.0 g (0.26 mole) of (2-(2- methoxytetrahydropyran-6-oxy)ethyl)-3-chloropropanoate in 230 ml of benzene was added 79.0 g (0.78 mole) of triethylamine. The solution was heated to 80° C. for 4 hours while sparging throughout with N$_2$. The reaction solution was divided into two equal portions; each was added to 200 ml of H$_2$O (pH 9) and extracted with two 100 ml portions of diethyl ether. The extracts were combined and dried over a mixture of magnesium sulfate and potassium carbonate. The dried solution was evaporated to give 22.42 g (91.4% yield) of crude product. A 27.0 g batch of crude Compound VI was vacuum distilled to give 18.0 g (66% yield) of at least 98% pure Compound VI. The slightly yellow-clear liquid had a boiling point of 108° C./0.05 mm Hg. The structure was in agreement with the following data:

IR: 2945, 1729, 1635, 1618, 1405, 1360, 1193, 1118, 1060, 1010, 945, 800 cm$^{-1}$;

$^{13}$C—NMR 166.91, 131.97, 130.18, 99.95, 98.71, 66.91, 65.12, 56.12, 31.53, 18.85 ppm. The latter also showed it to be a mixture of two (cis and trans) isomers.

EXAMPLE 5

Synthesis of 4-(2-methoxytetrahydropyran-6-oxy)methacrylanilide (VII)

Compound VII was made as follows: 8.85 g of p-hydroxymethacrylanilide was mixed with 34 g of 3,4-dihydro2-methoxy-(2H)pyran under an atmosphere of nitrogen. A drop of methanesulfonic acid was used to initiate the reaction. Over a two hour period, the reaction mixture slowly clarified and then rapidly turned into a solid mass of precipitate. The precipitate was dissolved in 170 ml of chloroform, extracted once with 200 ml of 0.1 N NaOH, and washed with 200 ml of H$_2$O. The organic phase was collected, dried over anhydrous MgSO$_4$, and filtered. Part of the chloroform was removed under reduced pressure until the volume was about 50 ml. The chloroform solution was then poured into 500 ml of hexane. The precipitate was collected and washed with hexane. After drying in a vacuum oven, the crude product yield was 10.5 g (72%). The crude product was redissolved in 100 ml of CHCl$_3$ and the solution poured into one liter of hexane. The mixture was allowed to stand for one hour. The precipitate was collected and dried in a vacuum oven to give a purer product. The yield was 7.67 g (53%). The structure was in agreement with the following data:

IR: 3335 (—NH—), 1654 (amide), 1020 (substituted tetrahyropyran ring) cm$^{-1}$;

$^{13}$C—NMR 168.0, 155.0, 142.2, 133.4, 123.0, 123.0, 120.7, 118.2, 118.2, 100.0, 976, 57.2, 31.3, 31.0, 20.0, 18.4 ppm.

EXAMPLE 6

Preparation of Homopolymers of Compound III

A homopolymer of Compound III was prepared as follows: 5.58 g of Compound III was added to 22.3 ml of 2-butanone under an atmosphere of nitrogen. Homopolymerization was initiated by adding 0.056 g 2,2'-azobis[2-methylpropanenitrile](AIBN) to the mixture and raising the temperature to 75° C. The reaction was allowed to proceed at 75° C. for 22 hours, with two additions of AIBN, each of 0.028 g, at 3 and 6 hours after the start of the reaction. The reaction was stopped by removing the heat and pouring the mixture into 250 ml of hexane. The white precipitate that formed was collected by decanting the solvent, washing three times with hexane, and drying in a vacuum oven at 45° C. for 4 hours. Yield of the homopolymer was about 79%.

EXAMPLE 7

Preparation of Homopolymer of Compound IV

Homopolymerization of Compound IV (5 g) was carried out in 2-butanone (45 ml), at 75° C. for 22 hours, with AIBN as the initiator under a nitrogen atmosphere. Three additions of AIBN were made: the first (0.05 g) was made at the beginning of the reaction, the second (0.05 g) was made 3 hours later, and the third addition (0.025 g) was made 3 hours after the second. The reaction was stopped by removing the heat and pouring the mixture into 500 ml of hexane. After decanting the solvent and washing two times with hexane, the white precipitate was dried in a vacuum oven at room temperature overnight. Yield of the homopolymer was about 75%.

EXAMPLE 8

Preparation of Copolymer

A Copolymer of Compound III and acrylic acid was prepared as follows: a reaction mixture containing 5.025 g of Compound III, 0.22 g of acrylic acid, 0.026 g of AIBN in 21 ml of 2-butanone, under an atmosphere of nitrogen, was heated to 75° C. and allowed to react for 3 hours. The heat was then removed and the reaction mixture was poured into 200 ml of hexane. After decanting the solvent, the white precipitate was washed three times with hexane and dried in a vacuum oven at 45° C. for 4 hours. Yield of the copolymer was about 73%.

EXAMPLE 9

Preparation of Copolymer

A copolymer of Compound IV and itaconic acid was prepared as follows: 1.30 g of itaconic acid was dissolved in 56 ml of 2-butanone under nitrogen. Compound IV (4.89 g) and 0.062 g of AIBN were added and the temperature was raised to 75° C. and the mixture allowed to react for 2 hours, followed by another addition of 0.031 g of AIBN. After two more hours, the heat was removed and the reaction mixture was poured into 450 ml of hexane. After decanting the solvent, a white precipitate was collected. The precipitate was washed twice with hexane and dried in a vacuum oven at room temperature overnight. The IR spectrum of the polymer showed the presence of unreacted itaconic acid. Therefore, the white powder (4.08 g) was stirred in 150 ml of water for a few minutes, collected by filtration, and dried in a vacuum oven at room temperature overnight. The final yield of the copolymer was 3.06 g (49%).

EXAMPLE 10

Preparation of Terpolymer

A terpolymer comprising (2-hydroxyethyl) methacrylate, (2-(2-methoxytetrahydropyran-6-oxy)ethyl)-2-methyl-2-propenoate (Compound IV), and acrylic acid, in an equimolar ratio, was made as follows: Compound IV (4.00 g, 0.016 mole) was added to 65.07 g of 2-butanone followed by (2-hydroxyethyl)methacrylate (2.08 g, 0.016 mole) and acrylic acid (1.23 g, 0.016 mole). The apparatus was flushed with N$_2$, as 40 mg of AIBN was added. The solution was heated at 75° C. for 3 hours. The clear, colorless solution was poured into 300 ml of hexane and the precipitate collected and vacuum dried overnight at room temperature. A hard white polymer was collected (2.82 g, 39.0% yield).

EXAMPLE 11

Preparation of Terpolymer

A terpolymer comprising (2-hydroxyethyl) methacrylate, (2-(2-methoxytetrahydropyran-6-oxy)ethyl)-2-propenoate (Compound VI) and acrylic acid, in an equimolar ratio was made as follows: Compound VI (4.00 g, 0.017 mole) was added to 66.96 g of 2-butanone, followed by (2hydroxyethyl)methacrylate (2.21 g, 0.017 mole) and acrylic acid (1.23 g, 0.017 mole). The solution was treated as described in Example 10. A hard, clear polymer (1.43 g, 19.2% yield) resulted.

EXAMPLE 12

Preparation of Tetrapolymer

A tetrapolymer containing Compounds III and IV was prepared as follows: Compound III (0.74 g, 0.004 mole) was added to 64 g of 2-butanone followed by the addition of 4.00 g (0.016 mole) of Compound IV, 2.08 g (0.016 mole) of (2-hydroxyethyl)methacrylate and 0.29 g (0.004 mole) of acrylic acid. The apparatus was flushed with N$_2$ as 71 mg of AIBN was added. The solution was heated to 75° C. and allowed to react for 3 hours. The reaction solution was then added to 300 ml of hexane causing precipitation of the polymer. The precipitate was vacuum dried at 25° C. and 0.1 mm Hg for 3 hours. A yellow, crystalline polymer was collected (1.72 g, 24.2% yield). The infrared spectroscopic analysis indicated the presence of a tetrahydropyran structure.

EXAMPLE 13

Preparation of Pentapolymer

A pentapolymer containing Compound III and Compound IV was prepared as follows: Compound III (1.49 g, 0.008 mole) was added to 109 g of 2-butanone followed by the addition of 4.00 g (0.016 mole) of IV, 1.38 g (0.016 mole) of methacrylic acid, 3.20 g (0.008 mole) of polyethylene glycol monomethyl ether methacrylate (MW 400) and 2.08 g (0.016 mole) of (2-hydroxyethyl)-methacrylate. As the apparatus was flushed with $N_2$, 122 mg of AIBN was added. The solution was allowed to react at 75° C. for 3 hours. The reaction solution was then added to 300 ml of hexane causing precipitation of the polymer. The polymer was dried at 25° C. and 0.1 mm Hg for three hours. A white, crystalline polymer was collected (4.9 g, 40% yield). The infrared spectroscopic analysis indicated the presence of a tetrahydropyran structure.

EXAMPLE 14

Microbiological Testing

Polymeric films for microbiological testing were prepared as follows: 200 mg of polymer was dissolved in 4 ml of acetone. The solution was poured into a 100×15 mm glass petri dish. The solvent was evaporated in a hood at 25° C.

The film was inoculated as follows: cells of a 24-hour culture of *Staphylococcus aureus* were spun down in a centrifuge and then resuspended in deionized water. A 0.1 ml inoculum of the suspension was spread onto the film. The dish was covered and stored in a humidity chamber to prevent drying of the inoculum.

After incubation at 25° C., 90-95% humidity, for a measured length of time, the film was swabbed with a 1×1 inch wet cotton swatch that was then added to 9 ml of letheen broth and vortexed. The letheen broth was appropriately diluted and plated out using Tryptone-Glucose-Yeast Extract agar (Difco Inc.) The control was an empty glass petri dish without the film.

The results are described in Tables 1 and 2 below.

TABLE I

| Polymer | Log Reduction (contact time) | |
|---|---|---|
| | 15 minutes | 1 hour |
| poly(III) | 0 | 0.3 |
| poly(III/ACA[1] = 2:1)[4] | 4 | >6 |
| poly(III/ACA = 9:1) | 1 | >6 |
| poly(III/ITCA[2] = 2:1) | >6 | >6 |
| poly(III/HEMA[3] = 1:1) | 2.6 | >6 |
| poly(III/HEMA = 2:1) | 2 | 5 |

[1]ACA = acrylic acid
[2]ITCA = itaconic acid
[3]HEMA = 2-hydroxyethyl methacrylate
[4]The numbers inside parentheses are found to correspond approximately to the actual ratios of incorporation into the copolymers.

TABLE 2

| Polymer | Log Reduction (contact time) | |
|---|---|---|
| | 1 hour | 24 hours |
| poly(IV) | 0 | 0.7 |
| poly(IV/ACA = 2:1) | 0 | 4.6 |
| poly(IV/ACA = 4:1) | 0 | 2.0 |
| poly(IV/ACA = 9:1) | 0 | 0.6 |
| poly(IV/ITCA = 2:1) | 1.3 | >6 |

Tables 1 and 2 show that polymers containing Compound III require very short contact times to achieve self-sanitization whereas those containing Compound IV require longer contact times. Each log reduction represents a 10-fold decrease in bacteria count.

EXAMPLE 15

Shower Testing of Film

Tests were conducted to determine if the surface coating films of the present invention still possessed antimicrobial activity after they had been showered with water. The test simulates the situation in which a surface coated with the polymer film is cleaned with a hose.

Onto each of a set of 11×11 cm glass tiles, a solution of 200 mg of polymer in 4-5 ml of acetone was poured. After the solvent had evaporated, hard and transparent films remained.

The tiles, held vertically in a rack, were exposed to a distilled water shower spray provided by a bar containing spray nozzles that produced an overlapping spray pattern at a rate of 1.5 gallons per hour. After specified lengths of time, the tiles were removed from the shower and allowed to air dry at room temperature while remaining in a vertical position.

The dried tiles were each inoculated with 1.0 ml of a 24 hour culture of *Staphylococcus aureus* (ATCC 6538) diluted in buffered water, which was spread evenly over the entire surface. After a 30 minute contact time at room temperature each tile was swabbed with a 1 in² cotton swatch wetted with sterile buffered water. The swatch was then added to 9 ml of neutralizer (1% sodium thiosulfate +1% peptone +0.1% sodium bisulfite, in deionized water) in a test tube. The tube was vortexed and the solution was plated out using appropriate dilutions on Tryptone-Glucose-Yeast Extract agar (Difco Inc.) The results are summarized in Table 3, below.

TABLE 3

| Copolymer | Log Reduction (Shower Exposure Time, minutes) | | | | | | | | |
|---|---|---|---|---|---|---|---|---|---|
| | 0.25 | 1 | 5 | 15 | 30 | 60 | 120 | 180 | 240 |
| (III/HEMA = 1:1) | 6.0 | 6.2 | 6.6 | 5.9 | 0.8 | 0.8 | 1.4 | 0.7 | 0.6 |
| (III/HEMA = 2:1) | 5.5 | 5.8 | 5.9 | 6.2 | 5.9 | 5.2 | 3.5 | 1.4 | 1.6 |

The results indicate that poly (III/HEMA =2:1) films provided residual antimicrobial activity even after two hours under shower conditions.

EXAMPLE 16

Hand Washing of Film

Tests were conducted to simulate cleaning by handwashing to determine if the polymer films of the invention retained antimicrobial activity after they had been hand-washed.

Films on 11×11 cm glass tiles were prepared by dissolving 200 mg of polymer in 4-5 ml of acetone, pouring the solution on the glass tile, and allowing the solvent to evaporate. The films so obtained were transparent and hard.

Each hand wash consisted in wiping the entire tile surface covered by a film with a wet soft paper towel in a back and forth motion twice. After the surface had been blotted dry, it was inoculated with 1 ml of a 24 hour culture of *Staphylococcus aureus* (ATCC 6538 diluted in buffer) which was spread over the surface. After a 30 minute contact time at room temperature the surface was swabbed with a wet 1 in² cotton swatch which was then added to a tube containing 9 ml of neutralizer (1% sodium thiosulfate +1% peptone +0.1% sodium bisulfite, in deionized water). The tube was vortexed and plated out using appropriate dilutions on Tryptone-Glucose-Yeast Extract agar, (Difco Inc.) The results are summarized in Table 4, below.

TABLE 4

| Copolymer | Log Reduction (Number of Hand-Washes) | | | | | | | |
|---|---|---|---|---|---|---|---|---|
| | 0 | 1 | 2 | 4 | 8 | 12 | 16 | 20 |
| (III/HEMA = 1:1) | 5.7 | 6.7 | 6.3 | 6.5 | >6.6 | >6.8 | 2.2 | 1.1 |
| (III/HEMA = 2:1) | 5.1 | 5.2 | 5.1 | 5.3 | >6.6 | 6.0 | 2.2 | 1.9 |

The results of Table 4 show that both polymer films have good residual antimicrobial activity even after 12 hand-washes, and therefore, can withstand cleaning by hand-washing.

The invention has been described in reference to various specific and preferred embodiments and techniques. However, it should be understood that many variations and modifications may be made while remaining within the spirit and scope of the invention.

What is claimed is:

1. An antimicrobial compound having the following general formula:

$$R-CH=C(R')-X-O-\text{[tetrahydropyran]}-OR'' \quad (I)$$

wherein
R = H, ($C_1$-$C_3$)alkyl, —COOH, —$CH_2$—COOH, —$C_6H_{11}$, or -phenyl;
R' = H, ($C_1$-$C_3$)alkyl, —$CH_2$—COOH, —$C_6H_{11}$ or -phenyl;
R'' = H or ($C_1$—$C_5$)alkyl; and X =

$$-\overset{O}{\underset{\|}{C}}-, \quad -\overset{O}{\underset{\|}{C}}-O+\overset{Z}{\underset{H}{C}}\!\!\nmid_{\overline{m}} \quad \text{or} \quad -\overset{O}{\underset{\|}{C}}-NH-\!\!\bigcirc\!\!-$$

where
m = 2–4; and
Z = H or ($C_1$-$C_3$)alkyl.

2. The compound of claim 1 wherein R = H or ($C_1$-$C_3$)alkyl.

3. The compound of claim 2 wherein R = H.

4. The compound of claim 1 wherein R' = H or ($C_1$-$C_3$)alkyl.

5. The compound of claim 4 wherein R' = H or —$CH_3$.

6. The compound of claim 1 wherein R'' = H or ($C_1$-$C_3$)alkyl.

7. The compound of claim 1 wherein X =

$$-\overset{O}{\underset{\|}{C}}- \quad \text{or} \quad -\overset{O}{\underset{\|}{C}}-O+\overset{Z}{\underset{H}{C}}\!\!\nmid_{\overline{m}}$$

where
m = 2; and
Z = H or ($C_1$-$C_3$)alkyl.

8. The compound of claim 7 wherein X =

$$-\overset{O}{\underset{\|}{C}}- \quad \text{or} \quad -\overset{O}{\underset{\|}{C}}-O+\overset{Z}{\underset{H}{C}}\!\!\nmid_{\overline{m}}$$

where
M = 2; and
Z = H or —$CH_3$.

9. The compound of claim 1 wherein R = H; R' = H or —$CH_3$; R'' = —$CH_3$; X =

$$-\overset{O}{\underset{\|}{C}}- \quad \text{or} \quad -\overset{O}{\underset{\|}{C}}-O+\overset{Z}{\underset{H}{C}}\!\!\nmid_{\overline{m}}$$

where
m = 2; and
Z = H or —$CH_3$.

10. A liquid composition comprising an effective antimicrobial amount of the compound of claim 1 dissolved in an organic solvent.

* * * * *